United States Patent [19]

Pennypacker et al.

[11] Patent Number: 4,817,622

[45] Date of Patent: Apr. 4, 1989

[54] INFRARED IMAGER FOR VIEWING SUBCUTANEOUS LOCATION OF VASCULAR STRUCTURES AND METHOD OF USE

[76] Inventors: Carl Pennypacker, 231 San Carlos, El Cerrito, Calif. 94530; Donald E. Morris, 44 Marguerita Rd., Kensington, Calif. 94707; Pieter P. Tans, 2960 13th St., Boulder, Colo. 80302

[21] Appl. No.: 888,916

[22] Filed: Jul. 22, 1986

[51] Int. Cl.[4] ............................................. A61B 5/00
[52] U.S. Cl. .................................... 128/664; 250/330; 358/113; 358/169
[58] Field of Search ............... 128/653, 664; 250/330, 250/342; 358/166, 167, 164, 169, 113

[56] References Cited

U.S. PATENT DOCUMENTS

| 3,566,669 | 3/1971 | Lawrence et al. | 250/330 |
|---|---|---|---|
| 3,583,223 | 6/1971 | Olsson | 250/330 |
| 3,635,085 | 1/1972 | Shimotsuma et al. | 250/330 |
| 3,798,366 | 3/1974 | Hunt et al. | 128/664 |
| 3,845,326 | 10/1974 | Godden | 358/164 |
| 3,969,571 | 7/1976 | Fenyo | 358/166 |
| 3,980,819 | 9/1976 | Schwartz | 358/166 |
| 4,063,093 | 12/1977 | Astheimer et al. | 250/330 |
| 4,080,532 | 3/1978 | Hopper | 250/330 |
| 4,323,973 | 4/1982 | Greenfield | 358/166 |
| 4,328,516 | 5/1982 | Colpack et al. | 250/330 |
| 4,388,729 | 6/1983 | Spencer et al. | 358/167 |
| 4,527,569 | 7/1985 | Kolb | 128/660 |
| 4,539,593 | 9/1985 | Jutier et al. | 358/166 |
| 4,598,314 | 7/1986 | Reimers | 358/140 |
| 4,618,928 | 10/1986 | Honda et al. | 358/167 |
| 4,623,923 | 11/1986 | Orbach | 358/166 |
| 4,626,905 | 12/1986 | Schmidt | 358/113 |
| 4,652,921 | 3/1987 | Rae-Smith | 358/166 |

OTHER PUBLICATIONS

Edrich et al., "Focussing Long-Wave Thermography" 14th Microwave Power Symposium 1979, Monaco Jan. 11-15, 1979, pp. 266-267.

Primary Examiner—Ruth S. Smith
Attorney, Agent, or Firm—Townsend and Townsend

[57] ABSTRACT

A human appendage, typically the inside of the elow, is illuminated with an infrared source, for example, at least one incandescent light bulb. A video camera for producing a video image and immediately overlying monitor for displaying the video image is utilized to look at the flesh. The camera is sensitive to infrared radiation. A video display results in which infrared absorbing or scattering contrasting portions of the flesh are highlighted, for example, hard to find veins for insertions of needles. A contrast enhancing circuit is included which discloses amplifying the video information with high contrast enhancement of the video. Adaptation of the disclosed circuit to conventional TV charge coupled device cameras and monitors is illustrated with compensation of horizontal sweep to even image background, intensity averaging line to line for vertical image uniformity and display of image contrasts on a log amplification format.

11 Claims, 3 Drawing Sheets

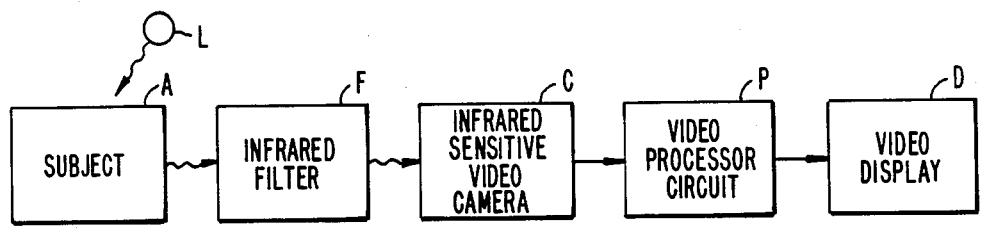
FIG._2.
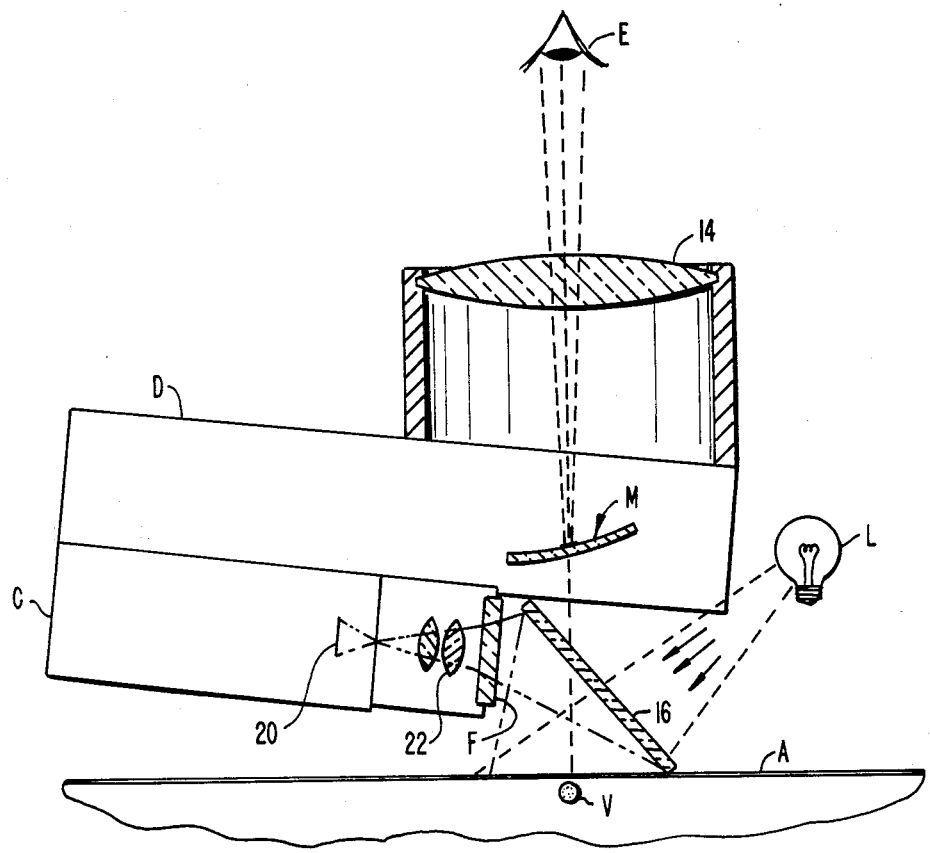
FIG._1A.
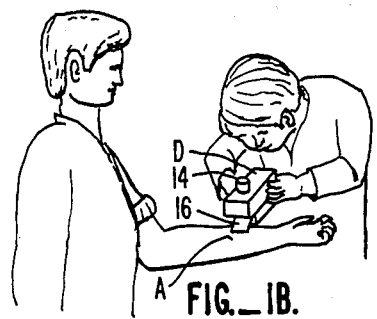
FIG._1B.

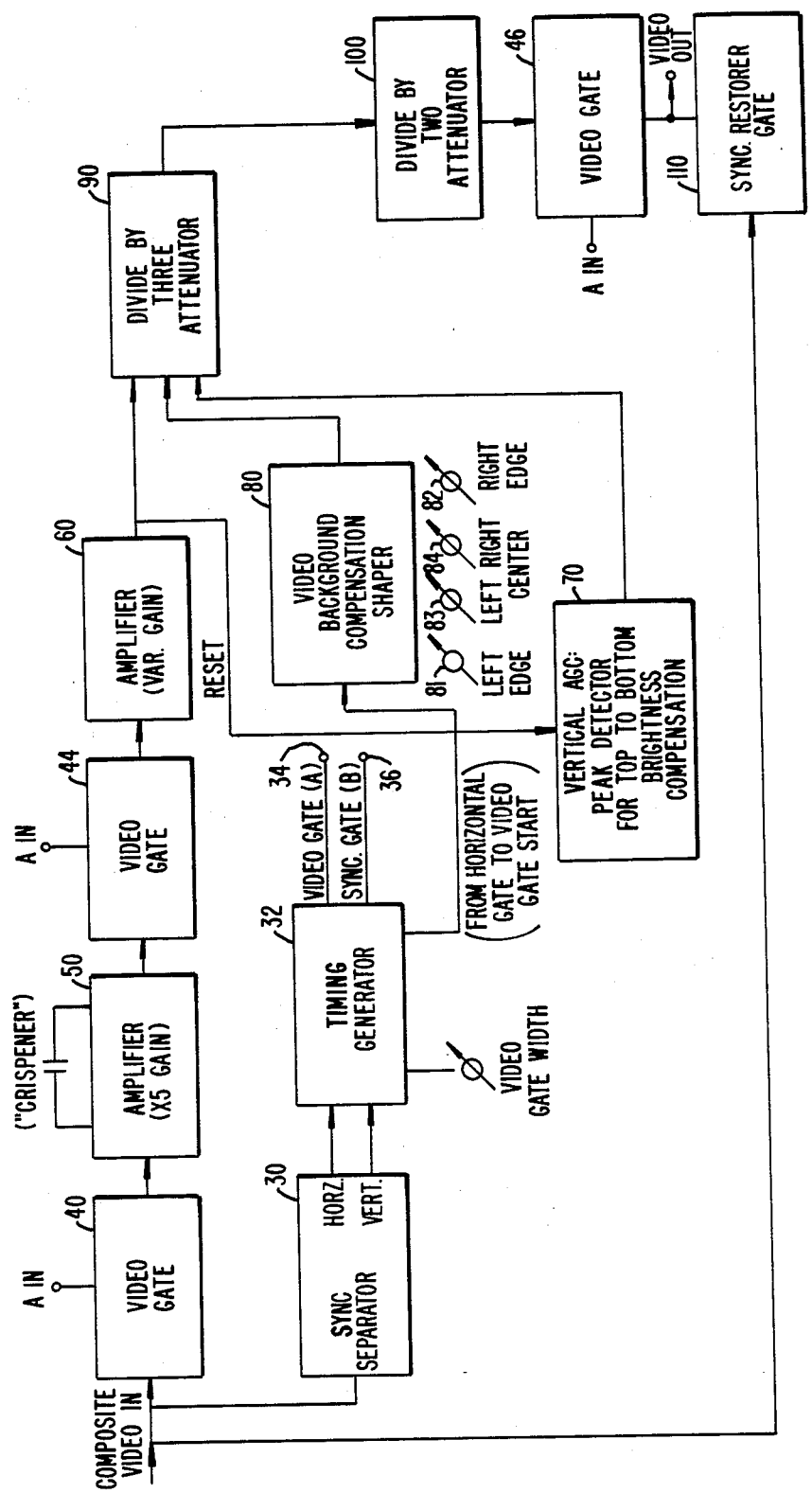
FIG._3.

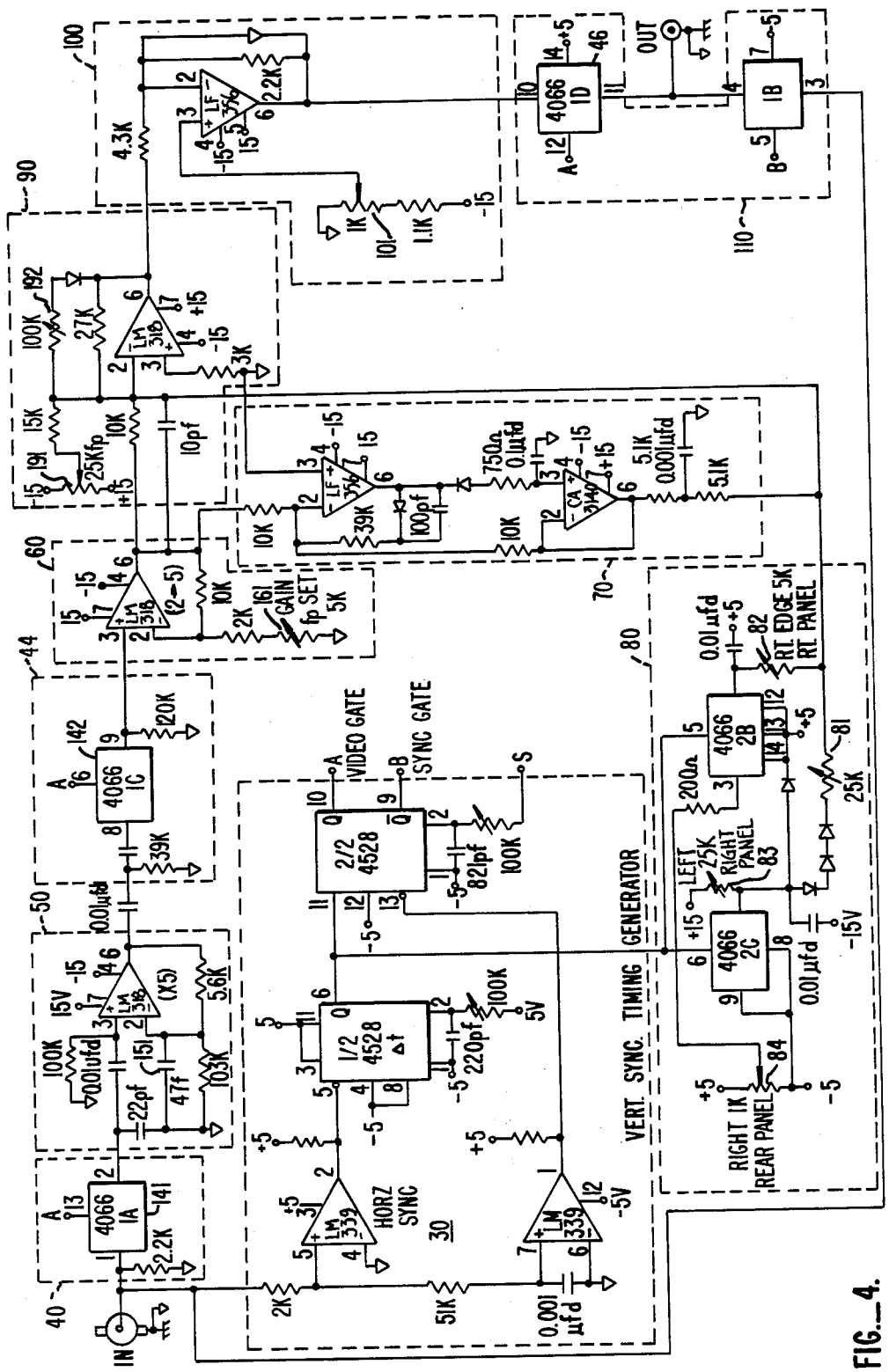
FIG._4.

INFRARED IMAGER FOR VIEWING SUBCUTANEOUS LOCATION OF VASCULAR STRUCTURES AND METHOD OF USE

BACKGROUND OF THE INVENTION

This invention relates to a simple, medical electronic device for viewing infrared absorption contrast under the skin. Simply stated, a TV camera and monitor is disclosed for viewing hard to find vascular structure for insertion of needles.

STATEMENT OF THE PROBLEM

Veins and arteries in many patients are hard to find. When dehydrated patients, dark-skin patients, and young patients are treated, finding the veins and arteries is a classic medical problem involving pain, stress and distress. Further, unskilled technicians have grave difficulty in locating many subcutaneous structures in even normal patients. Thus, an aid in locating such structures is needed.

STATEMENT OF THE RELEVANT ART

The use of infrared photography for visualizing subcutaneous veins, arteries and structures has been known for many years. These systems make use of the penetration of the near infrared rays into the skin, and the preferential absorption of the near infrared rays by the molecules in the vascular system. Consequently, a low contrast infrared image can be produced.

Heretofore, this technique has only been used with photography.

SUMMARY OF THE INVENTION

Part of the human body or appendage, for example the inside of the elbow, is illuminated with an infrared source, for example, at least one incandescent light bulb. A video camera for producing a video image and immediately overlying monitor for repeating the video image is utilized to look at the flesh. The video camera is sensitive to infrared radiation. If the camera is also sensitive to visible light, an infrared passing filter which stops visible light may be interposed. A video display results in which infrared contrasts in portions of the flesh are highlighted, for example, hard to find veins for insertions of needles. A contrast enhancing circuit is included which discloses amplifying the video information with high contrast enhancement of the video signal. Adaptation of the disclosed circuit to conventional CCD cameras and monitors is illustrated with compensation of horizontal sweep to even out image background, intensity averaging line to line for vertical image uniformity and display of image contrasts on a non-linear scale.

OTHER OBJECTS AND ADVANTAGES

An object of this invention is to disclose a process for finding infrared contrast differentiated structure in the flesh, for example veins in human appendages such as the inside elbow of the arm. A source of infrared illumination is provided, which for example can be a regular incandescent bulb, or an infrared light emitting diode or laser. An infrared sensitive video camera and immediately overlying video monitor for displaying the image from the camera is used. The video signal is enhanced as to contrast to display the underlying infrared absorption or scattering differentiated structure.

An advantage of the disclosed process and apparatus is that it is specifically suited for finding veins and arteries. Moreover, relative movement of a needle tip to a vein or artery is easily observed.

A further object of this invention is to disclose a process of video signal enhancement of an infrared image showing vascular structure. Simply, the video portion of the signal is amplified with an enhanced contrast output. Thereafter, the sync signal is added and played at a monitor to disclose the infrared absorption differentiated area. For example, veins in appendages can be clearly shown.

Yet another object of this invention is to disclose adjustments that can adapt conventional silicon CCD cameras and monitors to portray enhanced contrast images. According to this aspect of the invention the sync pulses are stripped. Amplification occurs and the sync pulses are restored. The signal level along each horizontal scan line is compensated for variations in the background, typically near the beginning and the end of the scan line. Vertical intensity averaging is utilized with each line being intensity averaged and being utilized to control the intensity of at least the following line. Enhanced contrast is displayed within a limited linear range, outside of which range the log of the amplified high contrast image is displayed. Moreover, the total brightness excursion provided is clamped to prevent "false" sync pulses. A coherent signal capable of displaying an enhanced infrared image results.

Over photography, the disclosed infrared video technique can be used in real time to study subjects at the infrared wavelengths. More importantly, the contrast enhancing technique possible with video signal processing includes a dynamic range and signal to noise ratio far superior to infrared photography. Coupled with the real time aspect of this invention, a superior apparatus and process is disclosed.

BRIEF DESCRIPTION OF THE DRAWINGS

Other objects, features and advantages of this invention can become more apparent after referring to the following specification and attached drawings in which:

FIG. 1A is a side elevation section of the camera and monitor utilized to amplify a vein in an arm for manipulation of a needle to the vein;

FIG. 1B is a perspective illustrating a technician utilizing the apparatus in FIG. 1A to locate a vein.

FIG. 2 is a block diagram of the invention;

FIG. 3 is a block diagram of the video processor circuit; and,

FIG. 4 is a diagram of an actual circuit utilized to practice the invention.

DESCRIPTION OF THE PREFERRED EMBODIMENTS

Referring to FIGS. 1A and 1B, a conventional video display D having a monitor screen M is illustrated. The screen is observed by an observer at eye E through a lens system 14. A mirror 16 deflects an image through an infrared bandpass filter F to a video camera C. It will be understood that the video camera C is conventional. Video camera C includes a charged coupled device 20 with a lens system 22. As an alternative to the lens 22, a coherent optical fiber bundle can be used for imaging into the plane of the charged-coupled-device. An appendage A having a vein V is illustrated. Illumination occurs from a light source L, schematically shown.

It will be seen that monitor screen M of display D immediately overlies the real-world location of the vein V. The lens 14 projects the screen and its image of the vein, as seen by the observer at position E, into the same plane in space as the actual vein and appendage. This enables a technician manipulating a needle to see in real spatial alignment a two-dimensional picture of the needle and vein without parallax error. The size of the image on M can be chosen such that the projected image as seen from E will be full size, after magnification by lens 14. Substantial assistance of manipulating the needle with respect to the vein results.

The reader will understand that here we show a video display D. The image could likewise be recorded and stored for record purposes.

Referring to FIG. 2 a block diagram is shown. Typically light L (preferably a regular incandescent bulb) illuminates the appendage A of the subject. The light passes through an infrared filter F to an infrared sensitive video camera C. The signal thereafter is passed through a processing circuit P to a video display D. It is the video display D which shows the site.

Having set forth this much, the circuit of FIG. 3 can be easily understood. A sync separator 30 strips out a sync signal. It passes the stripped signal to a timing generator 32. The generator outputs through video gate 34 and sync gate 36 signals. These respective signals are utilized to switch on and off amplification and processing to the video signal only with amplification of the sync and frame pulse being omitted. Respective video gates are located at 40, 44, and 46. When either a video gate signal at 34 is detected or a sync gate signal at 36 is detected, operation of the amplifiers is switched out of the circuit output. However, when the absence of the video gate and sync gate signals is present, amplification as disclosed occurs.

A so-called "crispener" amplifier 50 is utilized. This amplifier supplies amplification in the range of five times. Moreover, it is operative to increase relative gain for the high frequency portion of the signal. Thus, when the scanning raster undergoes rapid high frequency excursion—as in coming across a relatively low contrast vein B in an appendage A—amplifier 50 enhances or renders sharper the signal.

Variable gain at amplifier 60 is provided for optimizing the gain to the particular patient.

Stopping here, and with conventional TV cameras and monitors, it has been found that the enhanced contrast produces an extremely unsuitable contrasted image (nearly black at some areas and nearly white at others) across the totality of the video picture because of variations in illumination or reflectance of the skin or optical system efficiency across the image. Accordingly, it is necessary to average the signal from top scan to bottom scan, to adjust the video background relative to the horizontal sweep and additionally to display contrasts beyond a limited range as the log of the resultant contrast signal.

Referring to circuit 70, the average intensity of a preceding horizontal scan line is remembered. This average intensity is fed back to the following video line. This intensity is used to modulate the intensity of the following line so that the average is maintained. Thus, the signal is prevented from having undesirable vertical contrasts.

Additionally, it has been found that the signal varies as the raster sweeps horizontally. The variation produced is typically at the edges or shoulders of the picture. Accordingly, the width of the shoulder adjustment is adjusted at left center adjustment 83 and right center adjustment 84. The amount of adjustment provided is adjusted at left adjustment 81 and at right adjustment 82. Thus, the background is adjusted to a level where the contrasted image can be seen.

A divided by three attenuator 90 provides two functions. First, divide by three attenuator 90 includes a soft clamp of the resultant video signal to give brightness proportional to the logarithm of the enhanced contrast produced by amplifiers 50 and 60 when it exceeds the linear range for display by the monitors. Secondly, the resultant signal is reduced in intensity so that the video signal having the right contrast range for display at the monitor is provided.

Additionally, a divide by two attenuator 100 is utilized. This attenuator also includes a hard clamp which clamps the excursion of the video signal sufficiently below an excursion which would be recognized as either an end of frame or sync signal. By such clamping, a video signal is produced which can be played to a monitor.

Finally, and after signal processing, a sync restorer gate 110 is utilized. Gate 110 puts back into the amplified and processed signal the video and sync gating required for monitor display.

Those having skill in the video arts will recognized that the video processor circuit here is shown connecting a conventional camera to a conventional monitor. If the camera and monitor here disclosed is to be integrally designed, the video portion of the camera signal would not have the sync pulses added to the video portion, until full image processing had occurred or the sync signal would be fed by a separate wire to the monitor sync circuit. Here, however, because a camera that adds sync pulses is utilized, it is necessary to strip the signal during amplification. Likewise, and because a conventional monitor is used, it is required to add the sync signal back immediately before the signal is played at the monitor.

Turning to FIG. 4, the actual fabrication of the enhancement circuit can now be easily understood.

Referring to FIG. 4 the video gate 40 is illustrated having an analog switch 141. Crispener amplifier 50 is shown having a high frequency bandpass capacitor at 151 with an amplifier at 152. Amplification connections illustrated are conventional. Video gate 44 has an analog switch 142.

Variable gain amplifier 60 includes a variable gain control 161.

Divide by three circuit 90 includes variable potentiometer 191 for setting the soft clamp level and 192 for adjustment of the clamp rate about the desired logarithmic function.

Divide by two attenuator 100 includes a variable pot 101 for setting the level of the hard clamp for prevention of an amplified pulse from being confused with a sync pulse.

Sync restorer gate 110 is again an analog switch. The switching here is phased to allow the sync pulse to pass out of the circuit.

The video compensator 80 includes potentiometer 81, 82 for adjustment of the intensity of the edge correction. The edge width itself is adjusted by the respective potentiometers 83, 84.

Circuit 70 is a conventional circuit for comparison of the average intensity of an overlying horizontal scan to a current horizontal scan. Output to the divide by three attenuator at 90 occurs.

It will be understood that the disclosed signal processing technique is exemplary. For example, the enhancement of the contrast herein provided could be over a limited brightness range. By the expedient of adjusting the brightness to a uniform level, areas of contrast can be enhanced.

Similarly, image enhancement can be provided by a crispener circuit or differentiator circuit which could be tuned to enhance areas differing in brightness. Thus, tuning of the image produced can result in resolution displaying the desired vascular structure.

Likewise, illumination of the subject by infrared light of differing wavelengths with subtraction of the brightness signal resulting from illumination at one wavelength from the signal produced by illumination at the other wavelength can occur. Alternately, and by using by light of differing wavelengths, the ratios of brightness between the two wavelengths at each point in the picture can be compared and displayed on the monitor.

Moreover, illumination may be moved to deeper region in the body. For example, a fiber optic bundle placed in contact with the skin (or in a body cavity or oriface) can be utilized to guide the illuminating infrared energy. This fiber optic bundle will illuminate relatively deep vascular structures, which surface illumination would not reach. This would reduce surface scattering of IR which occurs when a bulb is used to illuminate the surface, and can improve image contrast.

Furthermore, pressure on the skin will collapse veins and empty them of blood, thus applying and removing pressure and subtracting the two images taken with and without pressure can enhance visibility of the veins in the image.

This device is well adapted for diverse uses in medical examinations, such as examination of the middle ear behind the ear drum, which is transparent to near infrared of appropriate wavelength. Other applications include examination of the subsurface structure of the mucous membrane surfaces such as nose, mouth, throat, trachea, esophagus, stomach, etc., and vagina and rectum. This device can be adapted for use as a real time infrared ophthalmoscope for examining behind the retina and for viewing the eye interior through cataracts.

We have illustrated the particular circuit here shown as a preferred embodiment. However, the enhancement of the infrared image to which we refer includes any of the above apparatus, the present method being preferred because of reduction of practice.

What is claimed is:

1. Apparatus for producing an enhanced contrast infrared image of the flesh for viewing subcutaneous structures such as veins in flesh illuminated with light which includes infrared light, said apparatus comprising:

light source means including means for providing infrared light and adapted to illuminate a portion of flesh so as to produce an image of said flesh from differential absorption of said infrared light on said flesh;

video camera means adapted to receive an image of said differentially absorbed infrared light on said illuminated flesh and output a video signal;

monitor means for playing back from said outputted video signal the image of said illuminated flesh; and, circuit means connecting said video camera means and said monitor means for producing an enhanced contrast image of said flesh in real time whereby said image from said differential absorption of infrared light has the contrast enhanced to view subcutaneous structure such as veins.

2. The apparatus of claim 1 and wherein said monitor means is located immediately overlying said camera means and oriented to display said image away from said camera means whereby said image in said monitor means overlies said flesh in space.

3. The apparatus of claim 1 wherein said circuit means includes means for generating successive horizontal scans and further includes means for vertically averaging the intensity of each horizontal scan to the intensity of at least one horizontal scan.

4. The apparatus of claim 3 and wherein said circuit means includes means for adjusting the background of said horizontal scans with respect to a corresponding scan of said camera means and monitor means.

5. The apparatus of claim 1 and wherein said circuit means includes means for amplifying the video signal of said camera profiled to a log output.

6. The invention of claim 5 and wherein said circuit means includes means for passing to high amplification, high frequency contrast signals in said video signal.

7. A process for viewing infrared absorbing or scattering structures in flesh, such as veins, comprising illuminating said flesh with an infrared light source to produce differential infrared absorption of infrared light;

taking an infrared video image, using a video camera, of said infrared illuminated flesh to produce a differential infrared absorption image of said illuminated flesh on a monitor;

outputting a video signal of said differential infrared absorption image of said illuminated flesh;

providing enhanced contrast amplification to the video signal derived from the infrared image of said flesh; and, playing back the video image of said flesh on a monitor to produce a high contrast visible image of infrared absorbing or scattering structures in said flesh in real time.

8. The process of claim 7 and including the step of positioning said monitor immediately overlying said camera and orienting said monitor to display said image away from said camera and the flesh whereby said image in said monitor overlies said flesh in space.

9. The process of claim 7 and including amplifying said video signal by preferably amplifying high frequency portions of said video signal to enhance said infrared absorbing or scattering structures.

10. The process of claim 7 and including in said amplification step vertically averaging each line of said video signal with respect to a previous line of said video signal.

11. The process of claim 7 and including in said amplification step adjustment of the horizontal background of said scan.

* * * * *